(12) United States Patent
Uchino et al.

(10) Patent No.: US 8,411,263 B2
(45) Date of Patent: Apr. 2, 2013

(54) METHOD OF EVALUATING SILICON WAFER AND METHOD OF MANUFACTURING SILICON WAFER

(75) Inventors: Shin Uchino, Tokyo (JP); Masataka Hourai, Tokyo (JP); Yasuo Koike, Tokyo (JP); Ryuji Ohno, Tokyo (JP)

(73) Assignee: Sumco Corporation, Tokyo (JP)

( * ) Notice: Subject to any disclaimer, the term of this patent is extended or adjusted under 35 U.S.C. 154(b) by 0 days.

(21) Appl. No.: 13/459,776

(22) Filed: Apr. 30, 2012

(65) Prior Publication Data

US 2012/0293793 A1    Nov. 22, 2012

(30) Foreign Application Priority Data

May 20, 2011    (JP) .................................. 2011-113173

(51) Int. Cl.
*G01N 21/94* (2006.01)
(52) U.S. Cl. .................................. 356/237.2; 356/237.4
(58) Field of Classification Search .... 356/237.2–237.6; 422/68.1, 82.01, 82.05, 82.07, 82.08, 82.09; 250/370.01; 436/172
See application file for complete search history.

(56) References Cited

FOREIGN PATENT DOCUMENTS

| JP | 6-18417 | 1/1994 |
| JP | 11-274257 | 10/1999 |
| JP | 2002-246429 | 8/2002 |
| JP | 2003-45928 | 2/2003 |

OTHER PUBLICATIONS

Buczkowski et al., "Photoluminescence Intensity Analysis in Application to Contactless Characterization of Silicon Wafers", Journal of the Electrochemical Society, Jun. 16, 2003, pp. G436-G442.

*Primary Examiner* — Tri T Ton
(74) *Attorney, Agent, or Firm* — Greenblum & Bernstein, P.L.C.

(57) ABSTRACT

A method of evaluating a silicon wafer includes obtaining first surface distribution information indicating an surface distribution of photoluminescence intensity on a surface of a silicon wafer; after obtaining the first surface distribution information, subjecting the silicon wafer to a thermal oxidation treatment, and then obtaining second surface distribution information indicating an surface distribution of photoluminescence intensity on the surface of the silicon wafer; obtaining difference information for the first surface distribution information and third surface distribution information, with the third surface distribution information having been obtained by correcting the second surface distribution information with a correction coefficient of less than 1; and based on the difference information obtained, evaluating an evaluation item selected from the group consisting of absence or presence of oxygen precipitates and surface distribution of oxygen precipitates in the silicon wafer being evaluated.

7 Claims, 8 Drawing Sheets

Fig. 4
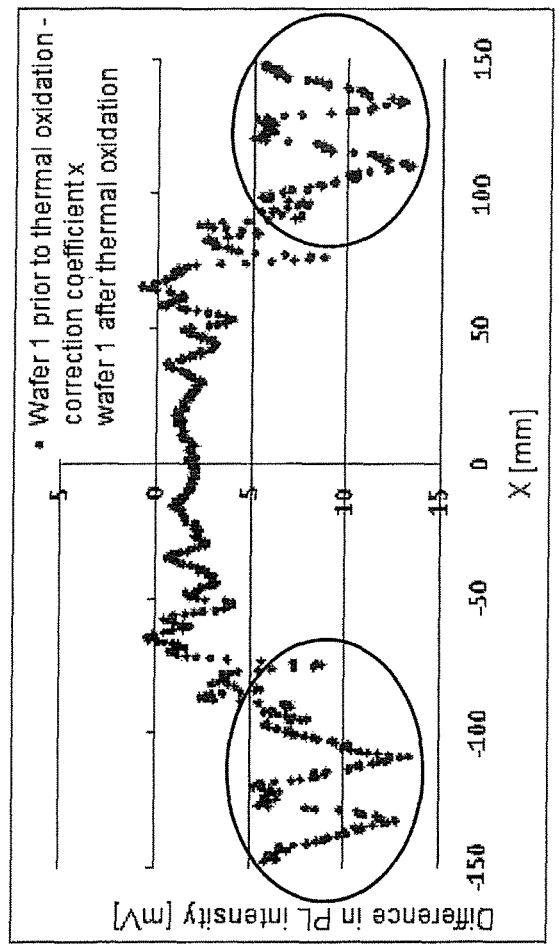
Difference image of wafer 1
= (Prior to thermal oxidation) −
correction coefficient x
(after thermal oxidation)
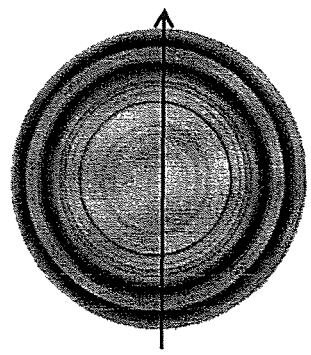

Fig. 5 Wafer 2
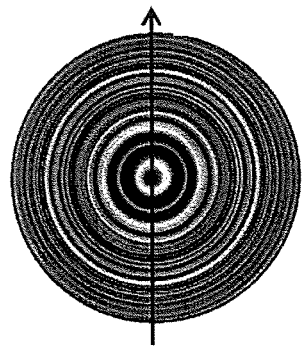
After thermal oxidation treatment
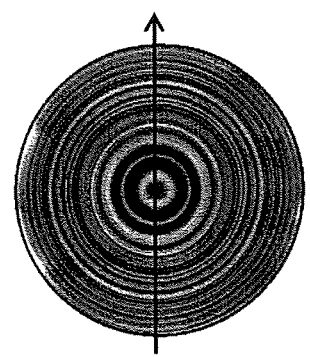
Prior to thermal oxidation treatment Fig. 7
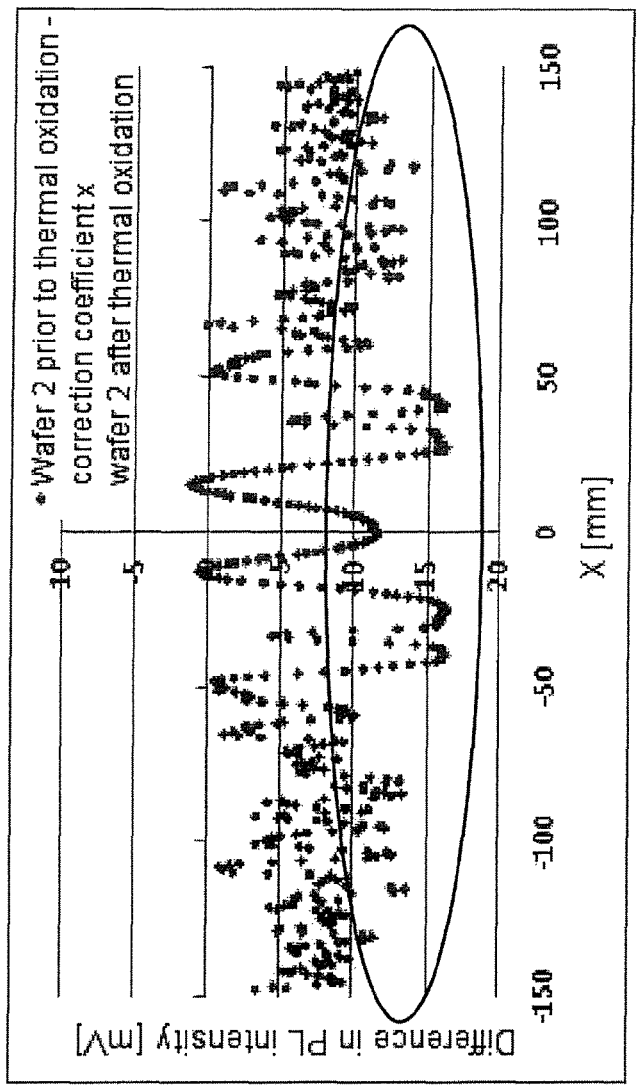
Difference image of wafer 2
= (Prior to thermal oxidation) −
correction coefficient x
(after thermal oxidation)
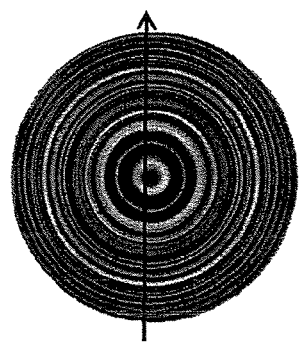

METHOD OF EVALUATING SILICON WAFER AND METHOD OF MANUFACTURING SILICON WAFER

CROSS-REFERENCE TO RELATED APPLICATIONS

This application claims the benefit of priority under 35 USC 119 to Japanese Patent Application No. 2011-113173, filed on May 20, 2011, which is expressly incorporated herein by reference in its entirety.

BACKGROUND OF THE INVENTION

1. Field of the Invention

The present invention relates to a method of evaluating a silicon wafer, and more particularly, to a method of evaluating a silicon wafer permitting evaluation of the absence or presence, and surface distribution, of oxygen precipitates in a silicon wafer utilizing photoluminescence.

The present invention further relates to a method of manufacturing a silicon wafer capable of providing a high-quality silicon wafer the quality of which is assured by the above evaluation method.

2. Discussion of the Background

When a silicon wafer containing oxygen precipitates is employed as a substrate of a semiconductor device and the oxygen precipitates are present in the active region of the device, they compromise device characteristics by lowering the dielectric strength voltage of gate oxide films, increasing the junction leak current, and the like. Additionally, when they are present in the bulk outside the active region of the device, they effectively serve as a gettering source, trapping heavy metal contamination that has mixed in during device processing. Accordingly, to fabricate high-quality devices, it is important to determine the absence or presence, and surface distribution, of oxygen precipitates in silicon wafers.

Infrared interference methods and infrared scattering methods have conventionally been employed as methods of evaluating oxygen precipitates in silicon wafers (for example, see Japanese Unexamined Patent Publication (KOKAI) No. 2002-246429, which is expressly incorporated herein by reference in its entirety).

In a silicon wafer of relatively high substrate resistivity, the substrate will have high infrared transmittance. Thus, it is possible to evaluate oxygen precipitates with high precision by methods utilizing infrared radiation. However, in low resistance p+ substrates and p/p+ silicon wafers (having a p-type epitaxial layer over a p+ substrate), the infrared transmittance of the substrate is low. Thus, in methods employing infrared radiation, evaluation of the absence or presence of interior defects in the form of oxygen precipitates, and their surface distribution, is difficult.

SUMMARY OF THE INVENTION

The present invention provides for a means for evaluating with high precision the absence or presence, and the surface distribution, of oxygen precipitates in silicon wafers regardless of substrate resistivity.

The present inventors conducted extensive research in that regard, resulting in the following new discoveries.

When electron-positive hole pairs are generated by directing onto a silicon wafer an excitation beam of greater energy than the band gap of silicon, light is emitted when the electron-positive hole pairs recombine. This phenomenon, called photoluminescence, has been utilized in recent years to evaluate semiconductor wafers (for example, see Reference A (Japanese Unexamined Patent Publication (KOKAI) No. 2003-45928), Reference B (Japanese Unexamined Patent Publication (KOKAI) Heisei No. 11-274257), Reference C (Journal of the Electrochemical Society, 150 (8) G436-G442, 2003), and Reference D (Japanese Unexamined Patent Publication (KOKAI) Heisei No. 6-18417), which are expressly incorporated herein by reference in their entirety).

As described in Reference A, when defects and contamination are present, corresponding electron levels are formed in the band gap. When these electron levels are present in the band gap, excited carriers recombine there, relatively reducing the ratio of light emitted due to direct recombination between bands. References A, B, and D utilize this phenomenon to provide methods of detecting internal defects such as heavy metal contamination and oxygen precipitates.

Accordingly, based on the descriptions in References A, B, and D and based on the surface distribution information on the intensity of photoluminescence (referred to as "PL intensity", hereinafter), the lower the PL intensity of a region, the greater the concentration of oxygen precipitates the region would conceivably be determined to have. However, the lower the resistivity, the greater the dependence of the PL intensity on substrate resistivity becomes. As shown in FIG. 7 of Reference C, when the substrate resistivity drops to equal to or lower than 0.1Ω·cm, the effect on the dependence of the PL intensity on resistivity increases, and it becomes difficult to evaluate with good precision the absence or presence, or the surface distribution, of oxygen precipitates based on the PL intensity.

Based on research by the present inventors, it has been determined that in low-resistivity substrates, it is sometimes difficult to evaluate the absence or presence, or surface distribution, of oxygen precipitates based on the PL intensity due to the following points.

The product name SiPHER made by BIO-RAD (which has now been purchased by Nanometrics) described in Reference A is a known measuring apparatus employed in the photoluminescence method (also referred to as the "PL method" hereinafter). This measuring apparatus is a device that maps the surface PL intensity of a wafer at room temperature. In the mapping profile that is obtained, regions of low PL intensity are shown dark (black) and regions of high PL intensity are shown bright (white). However, particularly in low-resistivity silicon wafers of high dopant concentration, nonuniformity in dopant concentration may produce variation in the surface resistivity. As a result, concentric circular fringe patterns (striations) sometimes appear in the mapping profile of the PL intensity. In mapping profiles in which such fringe patterns have appeared, it is difficult to determine whether the darkly displayed regions are regions where the PL intensity has decreased because of the presence of high concentrations of oxygen precipitates, or because of localized variation in resistivity.

By contrast, the present inventors noticed that:
(a) when a thermal oxidation treatment was conducted, surface recombination was inhibited, causing the PL intensity to rise over the entire surface of the silicon wafer;
(b) a heat treatment caused oxygen precipitates to grow (increase in size) in regions in which oxygen precipitates were present, so the PL intensity dropped; and
(c) the thermal oxidation treatment produced almost no change in dopant distribution.

Based on (a) to (c) above, regions in which the PL intensity dropped following thermal oxidation treatment could be determined to be regions in which oxygen precipitates were present. Further, although the overall PL intensity increased due to the thermal oxidation treatment, the distribution of the PL intensity due to the dependence of the PL intensity on resistivity and due to localized surface variation in resistivity could be deemed to essentially remain unchanged. Accordingly, by using a value of less than 1 correcting for the amount of the increase in PL intensity due to inhibiting of surface recombination as a correction coefficient and obtaining difference information on surface distribution information (such as a line profile and a mapping profile) of the photoluminescence intensity before and after thermal oxidation, it was possible to reduce or even eliminate the effects of the resistivity and the variation in surface resistivity, and evaluate the absence or presence, and surface distribution, of oxygen precipitates in the silicon wafer being evaluated.

The present invention was devised based on the above discoveries. The present invention can reduce or eliminate the effects of the dependence of the PL intensity on resistivity and variation in surface resistivity regardless of the level of substrate resistivity, and thus permit the evaluation of oxygen precipitates in silicon wafers.

An aspect of the present invention relates to a method of evaluating a silicon wafer, which comprises:

obtaining first surface distribution information indicating an surface distribution of photoluminescence intensity on a surface of a silicon wafer being evaluated;

after obtaining the first surface distribution information, subjecting the silicon wafer being evaluated to a thermal oxidation treatment, and then obtaining second surface distribution information indicating an surface distribution of photoluminescence intensity on the surface of the silicon wafer being evaluated;

obtaining difference information for the first surface distribution information and third surface distribution information, with the third surface distribution information having been obtained by correcting the second surface distribution information with a correction coefficient of less than 1; and based on the difference information obtained, evaluating an evaluation item selected from the group consisting of absence or presence of oxygen precipitates and surface distribution of oxygen precipitates in the silicon wafer being evaluated.

The silicon wafer may be a p+ wafer with a resistivity of equal to or lower than 0.1Ω·cm or a p/p+ wafer having a p-type epitaxial layer on a p+ substrate with a resistivity of equal to or lower than 0.1Ω·cm.

The correction coefficient may be a value calculated as [(standard photoluminescence intensity in the first surface distribution information)/(standard photoluminescence intensity in the second surface distribution information)].

The standard photoluminescence intensity may be a maximum photoluminescence intensity.

The surface distribution information may be a line profile or mapping profile of the photoluminescence intensity.

The photoluminescence intensity may be a band-edge luminescence intensity.

A further aspect of the present invention relates to a method of manufacturing a silicon wafer, which comprises:

preparing a silicon wafer lot containing multiple silicon wafers;

extracting at least one silicon wafer from the lot;

evaluating the silicon wafer that has been extracted by the method of evaluating a silicon wafer as set forth above; and shipping a silicon wafer as a product wafer, the silicon wafer being within the same lot as the extracted silicon wafer that has been determined to be non-defective in the evaluation.

Based on the present invention, it is possible to evaluate the absence or presence and surface distribution of oxygen precipitates regardless of the level of substrate resistivity of the silicon wafer that is being evaluated.

BRIEF DESCRIPTION OF THE DRAWINGS

The present invention will be described in the following text by the exemplary, non-limiting embodiments shown in the figure, wherein:

FIG. 2, right: after heat treatment) of the PL intensity before and after heat treatment in Example 1.

FIG. 4, left, is a difference image consisting of the mapping profile on the left in FIG. 2, from which the corrected mapping profile, obtained by multiplying the correction coefficient 0.67 with the PL intensity of the mapping profile shown on the right in FIG. 2, has been subtracted. FIG. 4, right, is the line profile of the PL intensity on the line indicated by the straight line with an arrow in the figure on the left.

FIG. 5 shows mapping profiles (FIG. 5, left: prior to heat treatment; FIG. 5, right: after heat treatment) of the PL intensity before and after heat treatment in Example 2.

FIG. 7, left, is a difference image consisting of the mapping profile on the left in FIG. 5 from which the corrected mapping profile, obtained by multiplying the correction coefficient 0.83 with the PL intensity of the mapping profile shown on the right in FIG. 5, has been subtracted. FIG. 7, right, is the line profile of the PL intensity on the line indicated by the straight line with an arrow in the figure on the left.

DETAILED DESCRIPTION OF THE EMBODIMENTS

Figure 1:
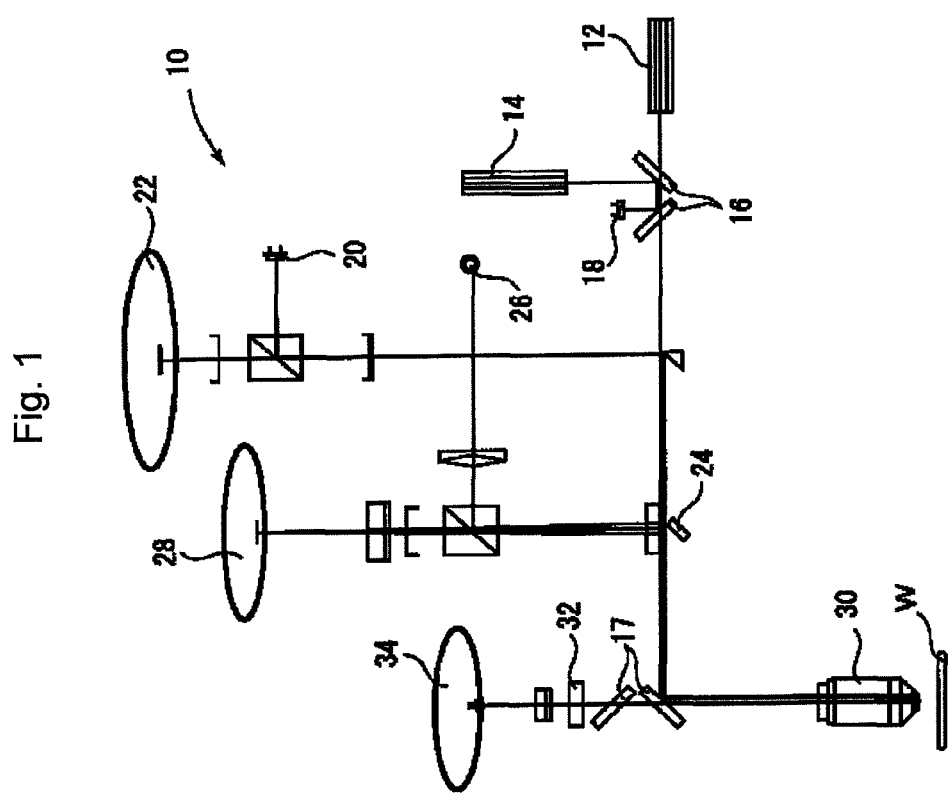
FIG. 1 is a schematic diagram of a measuring device based on the high-excitation microscopic photoluminescence method.

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The following preferred specific embodiments are, therefore, to be construed as merely illustrative, and non-limiting to the remainder of the disclosure in any way whatsoever. In this regard, no attempt is made to show structural details of the present invention in more detail than is necessary for fundamental understanding of the present invention; the description taken with the drawings making apparent to those skilled in the art how several forms of the present invention may be embodied in practice.

The present invention relates to a method of evaluating a silicon wafer. The evaluation method of the present invention comprises the following steps:

(1) obtaining first surface distribution information indicating an surface distribution of photoluminescence intensity on a surface of a silicon wafer being evaluated;
(2) after obtaining the first surface distribution information, subjecting the silicon wafer being evaluated to a thermal oxidation treatment, and then obtaining second surface distribution information indicating an surface distribution of photoluminescence intensity on the surface of the silicon wafer being evaluated;
(3) obtaining difference information for the first surface distribution information and third surface distribution information, with the third surface distribution information having been obtained by correcting the second surface distribution information with a correction coefficient of less than 1; and
(4) based on the difference information obtained, evaluating an evaluation item selected from the group consisting of absence or presence of oxygen precipitates and surface distribution of oxygen precipitates in the silicon wafer being evaluated.

The evaluation method of the present invention will be described in greater detail below.

Step (1)

In this step, first surface distribution information, indicating the surface distribution of the photoluminescence intensity on the surface of a silicon wafer being evaluated, is obtained. The surface distribution information obtained includes the effect of oxygen precipitates as well as the effects of localized variation in surface resistivity and dependence on resistivity in a low-resistivity substrate of high dopant concentration. Accordingly, steps (2) and beyond are implemented in the present invention to reduce or eliminate the effects of localized variation in surface resistivity and dependence on resistivity.

The measurement of the PL intensity in the present invention is not specifically limited so long as it is based on the photoluminescence method. From the perspective of simplicity of operation, the room-temperature photoluminescence method (room-temperature PL method), which does not require temperature controls, is desirable. In the room-temperature PL method, electron-positive hole pairs (that is, carriers), generated in the vicinity of the surface by an excitation beam of greater energy than the band gap of silicon that is caused to enter from the surface of the sample wafer surface, emit light and extinguish while diffusing into the interior of the wafer. The light that is emitted is called band-edge luminescence and exhibits a luminescence intensity with a wavelength of about 1.15 μm at room temperature (for example, 20 to 30° C.). Normally, in photoluminescence, visible light is employed as the excitation beam. Thus, if a light intensity with a wavelength of equal to or higher than 950 nm is measured as the PL intensity, it can be separated from the excitation beam. Thus, highly sensitive measurement is possible. In this regard, band-edge luminescence intensity is desirably measured as the PL intensity.

In the present invention, one example of a device that can be used to measure the PL intensity by the room-temperature PL method is a measuring device based on the high-excitation microscopic-photoluminescence method. The term "high-excitation microscopic-photoluminescence method" refers to the method using a visible light laser beam to excite carriers in silicon, and detecting the intensity of luminescence (band-edge luminescence) produced by the direct recombination of excited carriers between the band gaps. FIG. 1 is a schematic diagram of a measuring device based on the high-excitation microscopic-photoluminescence method. In the figure, 10 denotes the measuring device; 12 and 14 denote laser beam sources; 16 and 17 denote half mirrors; 18 denotes an output meter; 20 denotes a detector for surface-scattering light; 22 denotes a detector for autofocusing; 24 denotes a movable mirror; 26 denotes a white light source; 28 denotes a CCD camera; 30 denotes a microscope object lens; 32 denotes a longwave pass filter; 34 denotes a detector for photoluminescence light; and W denotes a sample being measured (silicon wafer). The sample being measured W is mounted on an X·Y stage, not shown. By moving the X·Y stage, it is possible to scan the excitation laser beam in the X and Y directions on the surface of the wafer. Thus, surface distribution information on the PL intensity is obtained for the silicon wafer being evaluated. The surface distribution information that is obtained can be a line profile or mapping profile of the PL intensity. To evaluate the absence or presence and distribution of oxygen precipitates over the entire surface region, it is desirable to obtain a mapping profile. In a mapping profile, the level of the PL intensity can be allocated to black-white brightness (degree of lightness), for example, to evaluate the level of the PL intensity based on the lightness of the mapping image.

Step (2)

It suffices for the thermal oxidation treatment in step (2) to be conducted under conditions that cause oxygen precipitates to grow and inhibit surface recombination. For example, the thermal oxidation treatment can be conducted by placing the silicon wafer for from about 30 minutes to 2 hours in a 100 percent oxygen atmosphere at about 750 to 1,000° C.

The PL intensity in the silicon wafer following the thermal oxidation treatment can be measured in the same manner as in step (1).

Step (3)

As set forth above, the PL intensity is decreased by growing oxygen precipitates in the region in which oxygen precipitates are present by the heat treatment of step (2). Although the PL intensity as a whole increases due to the inhibiting of surface recombination over the entire surface of the wafer, it is possible to view the PL intensity distribution caused by localized surface variation in resistivity and the dependence on resistivity of the PL intensity as essentially remaining unchanged before and after the thermal oxidation treatment. Accordingly, in the present invention, to correct for the amount of increase in PL intensity due to the inhibiting of surface recombination, a numeric value of less than 1 is employed as a correction coefficient. The difference information between the first surface distribution information and the third surface distribution information, the latter being obtained by multiplying the correction coefficient with the second surface distribution information [=the correction coefficient×(second surface difference information)], that is, [(first surface distribution information)−correction coefficient×(second surface distribution information)], is obtained. In the difference information thus obtained, the effects of the localized surface variation in resistivity and of the dependence on resistivity of the PL intensity are reduced or eliminated. Accordingly, in the difference information, oxygen precipitates can be determined to be present in regions in which a drop in PL intensity is observed. In this context, the value that is calculated as [(standard PL intensity in the first surface distribution information)/(standard PL intensity in the second surface distribution information)], is desirably employed as the correction coefficient for conducting suitable correction. The maximum PL intensities in the first and second surface distribution information can be employed as the standard PL intensities, or some other standard PL intensity, such as the average PL intensity, can be employed. The third surface distribution information and the above difference information can be readily obtained by inputting the correction coefficient to the program that is built into the measuring device employed to measure the PL intensity, or using a suitable program.

Step (4)

As set forth above, the surface regions of the wafer in which the PL intensity drops in the difference information obtained in step (3) are the regions in which the PL intensity has dropped due to the growth of oxygen precipitates caused by the thermal oxidation treatment, that is regions in which oxygen precipitates are present. Accordingly, the absence or presence of oxygen precipitates in the silicon wafer being evaluated can be evaluated based on whether or not regions of decreased PL intensity are present in the difference information. Further, the distribution of regions in which oxygen precipitates are present in the surface of the wafer can be evaluated based on the distribution of regions in which the PL intensity has dropped.

Based on the present invention as set forth above, the absence or presence, and the surface distribution, of oxygen precipitates in a silicon wafer can be evaluated with high precision by a PL method regardless of the level of substrate resistivity. The evaluation method of the present invention is desirably applied to silicon wafers of low substrate resistivity in which the effect due to the dependence of the PL intensity on resistivity and the effect due to localized variation in surface resistivity tend to be pronounced. Its application to p+ wafers with a resistivity of equal to or lower than 0.1Ω·cm, and to p/p+ wafers having a p-type epitaxial layer on a p+ substrate with a resistivity of equal to or lower than 0.1Ω·cm, is preferred.

The present invention further relates to a method of manufacturing a silicon wafer, which comprises the following steps: preparing a silicon wafer lot containing multiple silicon wafers; extracting at least one silicon wafer from the lot; evaluating the silicon wafer that has been extracted by the evaluation method of the present invention; and shipping a silicon wafer as a product wafer, the silicon wafer being within the same lot as the extracted silicon wafer that has been determined to be non-defective in the evaluation.

As set forth above, the absence or presence and the surface distribution of oxygen precipitates in the silicon wafer can be evaluated with high precision regardless of the substrate resistivity by the evaluation method of the present invention. Accordingly, it is possible to provide product wafers with high reliability that can be used to fabricate high-quality devices by shipping a silicon wafer, as a product wafer, in the same lot as a silicon wafer that has been determined by the above evaluation method to be a non-defective product which permits the manufacturing of a high-quality device with regard to the absence or presence, or surface distribution, of oxygen precipitates. The standard for determining a non-defective product can be established taking into account the physical properties that are required of the wafer based on the use and the like of the wafer. The number of wafers and the number of wafers extracted per lot can be suitably established.

EXAMPLES

The present invention will be described in detail below based on examples. However, the present invention is not limited to the examples. The "percent" given in Examples is weight percent.

Example 1

Figure 2:
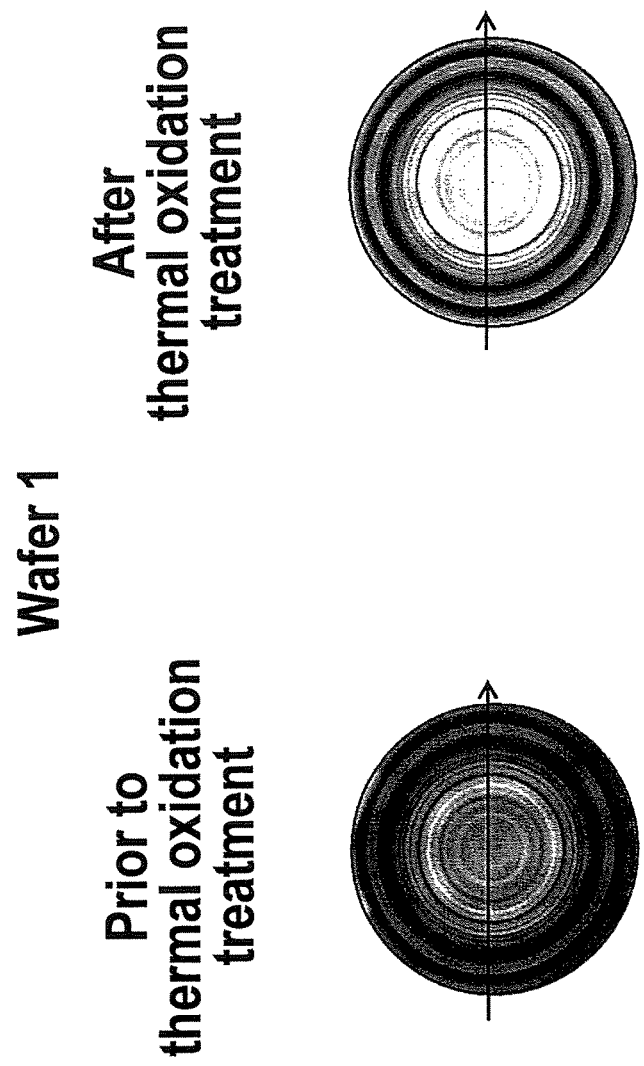
FIG. 2 shows mapping profiles (FIG. 2, left: prior to heat treatment.

The mapping profile (first surface distribution information), shown on the left in FIG. 2, of the surface that was to serve as the device fabrication surface of a wafer 1 in the form of a p+ substrate having a resistivity falling within a range of $5/1000$ to $10/1000$ Ω·cm was obtained by conducting band-edge photoluminescence emission intensity Map measurement at a resolution of 1 mm. In the measurement, a SiPHER PL measuring device from Nanometrics was employed as the device shown in FIG. 1 and a light source with a wavelength of 532 nm was employed as the measurement laser. In the mapping profile, portions of low PL intensity are shown dark (black) and regions of high intensity are shown bright (white). As shown on the left in FIG. 2, a concentric circular fringe pattern appeared due to localized variation in resistivity in the mapping profile. Thus, it was difficult to determine the absence or presence and distribution state of oxygen precipitates based on brightness.

Following the above PL measurement, wafer 1 was thermal oxidation treated by being placed for 60 minutes in a heat treatment furnace (atmospheric temperature within the furnace: 900° C., atmosphere within the furnace: 100 percent oxygen), after which Map measurement identical to that above was conducted to obtain the mapping profile (second surface distribution information) shown on the right in FIG. 2.

Figure 3:
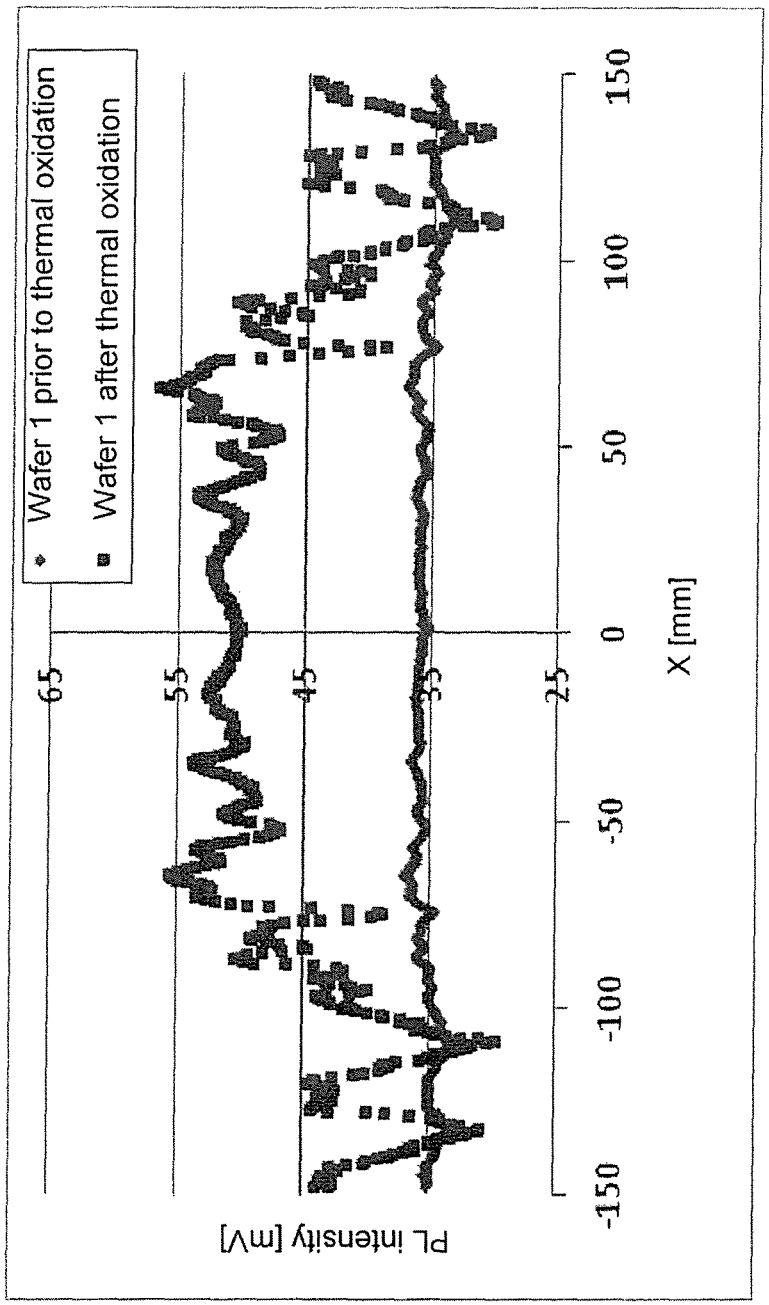
FIG. 3 is a line profile of PL intensity on the line indicated by straight lines with arrows in FIG. 2.

The line profile of the PL intensity on the line indicated by the straight line with the arrow in FIG. 2 is shown in FIG. 3. The fact that the PL intensity dropped in the peripheral region of the wafer was confirmed. The effect of the dependence of the PL intensity on resistivity and that of localized surface variation in resistivity were also present. However, if the mapping profile following the thermal oxidation treatment was simply subtracted from the mapping profile prior to thermal oxidation treatment and the difference image taken, the amount of increase in the PL intensity due to the inhibition of surface recombination due to thermal oxidation treatment would have ended up being included.

Accordingly, in the present Example, the maximum PL intensities measured on wafer 1 before and after thermal oxidation treatment were employed to calculate a correction coefficient for the correction of the above amount of increase. The "maximum PL intensity before thermal oxidation treatment/maximum PL intensity after thermal oxidation treatment" was calculated to be 0.67.

The PL intensity on the mapping profile shown on the right in FIG. 2 (the second surface distribution information) was multiplied by 0.67 to obtain a corrected mapping profile (third surface distribution information), which was then subtracted from the mapping profile (first surface distribution information) shown on the left in FIG. 2 to obtain the difference image shown on the left in FIG. 4. The figure on the right in FIG. 4 is the line profile of the PL intensity on the line indicated by a straight line with an arrow on the left in FIG. 4.

Example 2

Figure 6:
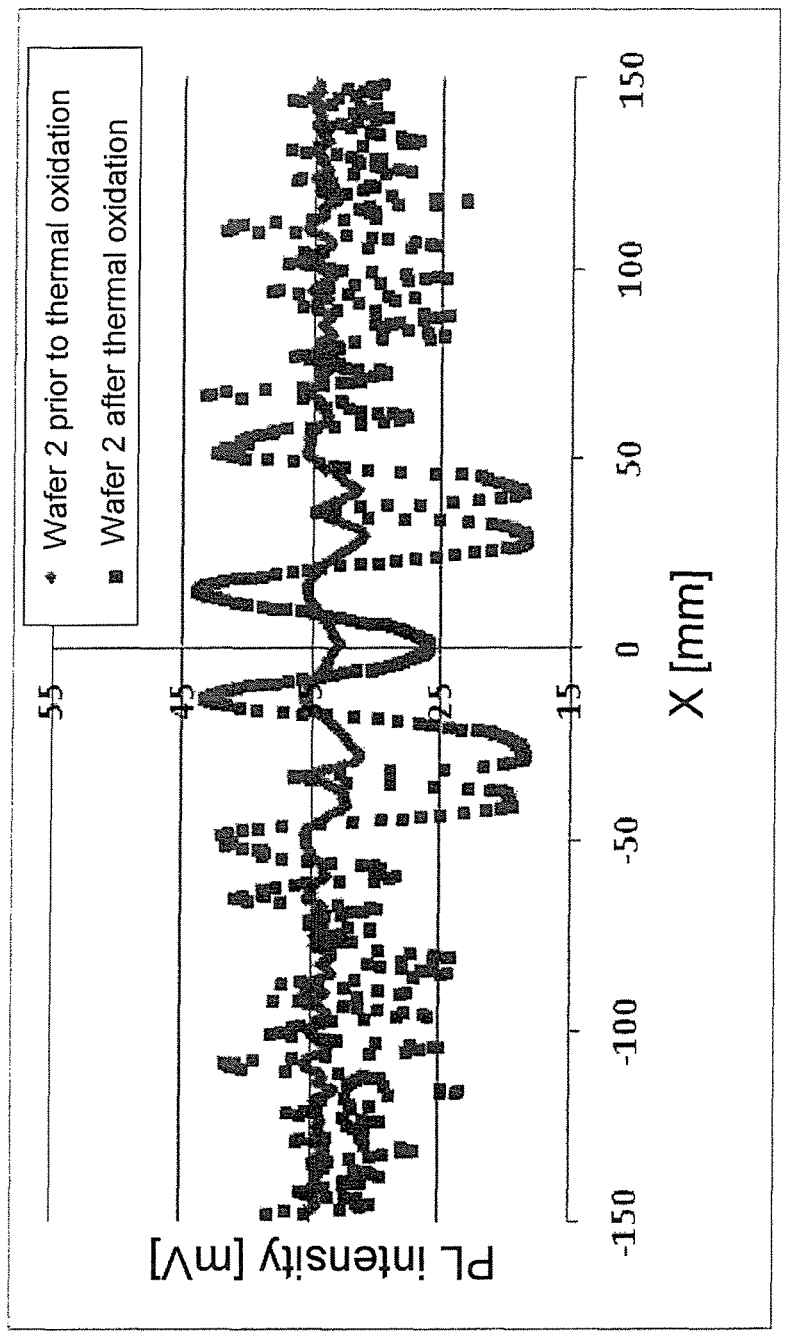
FIG. 6 is a line profile of the PL intensity on the lines with arrows in FIG. 5.

A wafer 2 in the form of a p+ substrate with a resistivity ranging from 5/1000 to 10/1000 Ω·cm was employed as the wafer being evaluated and measurements and evaluation identical to those in Example 1 were conducted. FIG. 5, on the left, shows the mapping profile prior to thermal oxidation treatment (the first surface distribution information), and FIG. 5, on the right, shows the mapping profile after thermal oxidation treatment (second surface distribution information). FIG. 6 is the line profile of the PL intensity on the line indicated by a straight line with an arrow in FIG. 5. The "maximum PL intensity prior to thermal oxidation treatment/maximum PL intensity after thermal oxidation treatment" was calculated as 0.83 for wafer 2. The PL intensity on the mapping profile shown on the right in FIG. 5 (the second surface distribution information) was multiplied by 0.83 to obtain a corrected mapping profile (third surface distribution information), which was then subtracted from the mapping profile (first surface distribution information) shown on the left in FIG. 5 to obtain the difference image shown on the left in FIG. 7. The figure on the right in FIG. 7 is the line profile of the PL intensity on the line indicated by a straight line with an arrow on the left in FIG. 7.

Figure 8:
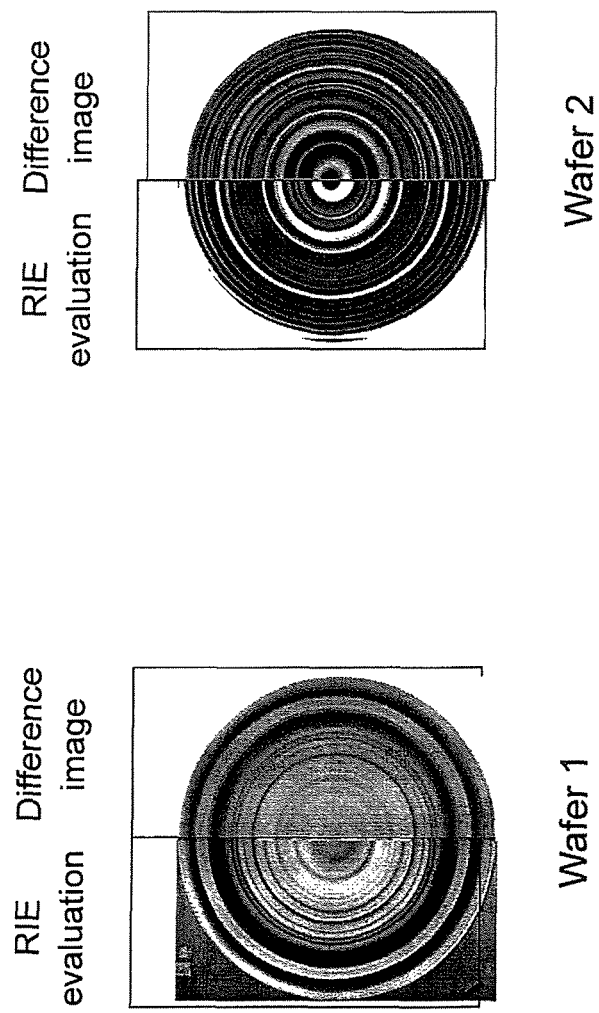
FIG. 8 shows a comparison of the results of the difference image with the evaluation results by RIE evaluation in Examples 1 and 2.

The regions displayed darkly in the figure on the left in FIG. 4 and the figure on the left in FIG. 7 are regions in which a drop in PL intensity was observed in the difference image. These regions correspond to the circled portions in the line profiles of the figures on the right of these same figures. To demonstrate that the regions in which a drop in PL intensity was observed in the difference images corresponded to regions in which oxygen precipitates were present, the results of RIE evaluation of wafers 1 and 2 following the evaluation of Examples 1 and 2 above are shown in FIG. 8. The RIE evaluation was conducted by the following method.

First, the wafer surface was etched to a depth of 3 μm with an aqueous solution of hydrofluoric acid and nitric acid, and the wafer surface was washed and dried. Subsequently, reactive ion etching was conducted. The reactive ion etching was conducted using a Magnetron RIE device (Precision 5000 ETCH, made by Applied Materials) under conditions of a high Si/SiO$_2$ selection ratio, that is, under conditions where SiO$_2$ tended not to be etched. This revealed oxygen precipitates (silicon oxide) as acicular protrusions. A mixed gas of HBr and O$_2$ was employed as the etching gas. The conditions were then set to obtain a Si/SiO$_2$ selection ratio of 120. Following reactive ion etching, washing was conducted with a hydrofluoric acid aqueous solution to remove the reaction products that had adhered during reactive ion etching, and a scattered light image of the surface of the wafer that had been etched by reactive ion etching was obtained using CCDs.

In RIE evaluation, the brightness is known to indicate the distribution of oxygen precipitates. Regions of low brightness (black) are regions in which oxygen precipitates are present at high concentration. As shown in FIG. 8, since the brightness distribution in the difference image corresponded well to the RIE evaluation results, the regions of low PL intensity (regions displayed darkly) in the difference image were confirmed to be regions in which oxygen precipitates were present.

The above results indicated that the present invention permitted the evaluation of the absence or presence and surface distribution of oxygen precipitates in silicon wafers by the PL method regardless of substrate resistivity.

The present invention is useful in the field of manufacturing semiconductor devices.

Although the present invention has been described in considerable detail with regard to certain versions thereof, other versions are possible, and alterations, permutations and equivalents of the version shown will become apparent to those skilled in the art upon a reading of the specification and study of the drawings. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any Examples thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method of evaluating a silicon wafer, which comprises:
    obtaining first surface distribution information indicating an surface distribution of photoluminescence intensity on a surface of a silicon wafer being evaluated;
    after obtaining the first surface distribution information, subjecting the silicon wafer being evaluated to a thermal oxidation treatment, and then obtaining second surface distribution information indicating an surface distribution of photoluminescence intensity on the surface of the silicon wafer being evaluated;
    obtaining difference information for the first surface distribution information and third surface distribution information, with the third surface distribution information having been obtained by correcting the second surface distribution information with a correction coefficient of less than 1; and
    based on the difference information obtained, evaluating an evaluation item selected from the group consisting of absence or presence of oxygen precipitates and surface distribution of oxygen precipitates in the silicon wafer being evaluated.

2. The method of evaluating a silicon wafer according to claim 1, wherein the silicon wafer is a p+ wafer with a resistivity of equal to or lower than 0.1Ω·cm or a p/p+ wafer having a p-type epitaxial layer on a p+ substrate with a resistivity of equal to or lower than 0.1Ω·cm.

3. The method of evaluating a silicon wafer according to claim 1, wherein the correction coefficient is a value calculated as [(standard photoluminescence intensity in the first surface distribution information)/(standard photoluminescence intensity in the second surface distribution information)].

4. The method of evaluating a silicon wafer according to claim 3, wherein the standard photoluminescence intensity is a maximum photoluminescence intensity.

5. The method of evaluating a silicon wafer according to claim 1, wherein the surface distribution information is a line profile or mapping profile of the photoluminescence intensity.

6. The method of evaluating a silicon wafer according to claim 1, wherein the photoluminescence intensity is a band-edge luminescence intensity.

7. A method of manufacturing a silicon wafer, which comprises:
- preparing a silicon wafer lot containing multiple silicon wafers;
- extracting at least one silicon wafer from the lot;
- evaluating the silicon wafer that has been extracted by the method of evaluating a silicon wafer according to claim 1; and
- shipping a silicon wafer as a product wafer, the silicon wafer being within the same lot as the extracted silicon wafer that has been determined to be non-defective in the evaluation.

* * * * *